United States Patent
Kiminami et al.

(10) Patent No.: US 9,205,232 B2
(45) Date of Patent: Dec. 8, 2015

(54) BALLOON FOR CATHETER AND BALLOON CATHETER

(75) Inventors: Hideaki Kiminami, Fujinomiya (JP); Hiromasa Kohama, Ashigarakami-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 573 days.

(21) Appl. No.: 13/554,717

(22) Filed: Jul. 20, 2012

(65) Prior Publication Data

US 2013/0085519 A1 Apr. 4, 2013

(30) Foreign Application Priority Data

Sep. 29, 2011 (JP) ................................ 2011-214484

(51) Int. Cl.
*A61M 29/00* (2006.01)
*A61M 25/10* (2013.01)
*A61L 29/06* (2006.01)
*A61L 29/08* (2006.01)
*A61L 29/18* (2006.01)

(52) U.S. Cl.
CPC ............. *A61M 25/10* (2013.01); *A61L 29/06* (2013.01); *A61L 29/085* (2013.01); *A61L 29/18* (2013.01)

(58) Field of Classification Search
CPC ..... A61L 29/06; A61L 29/0085; A61L 29/18; C08L 77/12; A61M 25/10; A61M 25/1002; A61M 25/1006; A61M 25/1009; A61M 25/1011; A61M 25/104; A61M 2025/105–2025/1097; A61M 2025/09008; A61M 3/0295; A61M 29/02; A61B 1/00082; A61B 5/6853; A61B 17/12022; A61B 17/12136; A61B 2017/12081; A61B 2017/22048; A61B 2017/22051–2017/22071; A61B 2017/320048; A61F 2/958; A61F 2/2433; A61F 2002/9583; A61F 2002/9586; A61F 2002/011
USPC ................. 606/194, 192; 604/103.06–103.08
See application file for complete search history.

(56) References Cited

U.S. PATENT DOCUMENTS

| | | | |
|---|---|---|---|
| 4,899,521 A | 2/1990 | Havens | |
| 5,270,086 A | 12/1993 | Hamlin | |
| 5,879,369 A * | 3/1999 | Ishida | ............................ 606/194 |
| 5,908,406 A * | 6/1999 | Ostapchenko et al. | .... 604/96.01 |
| 6,200,290 B1 * | 3/2001 | Burgmeier | ................. 604/96.01 |
| 7,247,147 B2 * | 7/2007 | Nishide et al. | ............. 604/103.1 |
| 2010/0174235 A1 * | 7/2010 | Yamaguchi | .............. 604/103.08 |
| 2010/0249824 A1 * | 9/2010 | Kishida et al. | ................. 606/194 |

FOREIGN PATENT DOCUMENTS

| | | |
|---|---|---|
| JP | 1-121362 A | 5/1989 |
| JP | 3-205064 A | 9/1991 |
| JP | 9-164191 A | 6/1997 |
| JP | 9-509860 A | 10/1997 |
| JP | 2001-516621 A | 10/2001 |
| WO | WO 95/23619 | 9/1995 |
| WO | WO 99/13924 A2 | 3/1999 |
| WO | WO 2008/023696 A1 | 2/2008 |

OTHER PUBLICATIONS

Office Action issued by the Japanese Patent Office in corresponding Japanese Patent Application No. 2011-214484 on Jul. 14, 2015 (3 pages).

\* cited by examiner

*Primary Examiner* — Jonathan W Miles
*Assistant Examiner* — Lucas Paez
(74) *Attorney, Agent, or Firm* — Buchanan, Ingersoll & Rooney PC (57) ABSTRACT

A balloon for catheter of the type that has a film body that is inflatable and deflatable using a fluid supplied from a catheter, the film body including a hard layer containing a polyamide and a flexible layer formed on the hard layer and containing a polyamide elastomer having a Shore D hardness that is not larger than 62, and the content of the amide units of the polyamide elastomer in the flexible layer is not less than 60 wt %.

18 Claims, 3 Drawing Sheets

BALLOON FOR CATHETER AND BALLOON CATHETER

CROSS-REFERENCE TO RELATED APPLICATION

This application claims priority under 35 U.S.C. §119 to Japanese Patent Application No. 2011-214484 filed in Japan on Sep. 29, 2011, the entire contents of which are hereby incorporated by reference.

FIELD OF THE INVENTION

Disclosed is a balloon for a catheter and a balloon catheter. Disclosed is a balloon used for insertion into a body cavity, and a balloon catheter used for insertion into a body cavity.

BACKGROUND DISCUSSION

A catheter attached to a balloon (for example, a balloon catheter) can be employed in a biological organ dilating method of placing a stent in a stenosis of the blood vessel or body cavity (for example, a biological lumen such as biliary duct, esophagus, trachea, urethra or the like) to secure a body cavity space. A catheter attached to a balloon can be employed in the therapy of ischemic heart disease or the urethral catheterization of a patient who has difficulty in urination. A method can be employed which includes expanding an affected area (stenosis) of the coronary artery or the urethral catheterization by passing from the urethral opening to the bladder. Such a balloon catheter includes a body shaft, an inflatable and deflatable balloon attached to the vicinity of the distal end portion of the shaft, and a hub attached to the base of the shaft.

The inflatable and deflatable balloon catheter can have characteristics including trackability (following performance of the balloon against a tortuous blood vessel or body cavity), capability of passage into a stenosis such as of a blood vessel, dilatability of a stenosis such as of a calcified blood vessel or the like. It can be desirable for the catheter balloon to have flexibility, thinning capability and high strength.

For such a balloon, materials can be used such as polyethylene terephthalate, polyolefins, polyamides and the like. Since polyethylene terephthalate is a high-strength material, a thinned balloon can be formed therefrom in order to increase trackability. There is a concern that when contacted with a calculus or a calcified affected part, the thinned balloon may be formed with pinholes, resulting in the breakage of the balloon in a body cavity or blood vessel. On the other hand, when the balloon is formed excessively thick, the flexibility and trackability of the balloon can be impaired although press capacity is ensured.

Polyolefins can be heat-sealed to the shaft and show flexibility and thus can be processed. Nevertheless, they can be relatively low in pressure resistance and can have such a tendency that the balloon diameter greatly changes relative to a change in balloon inflating pressure. Therefore, when a high pressure is exerted on the balloon, the balloon can sharply become enlarged, with the concern that a body cavity may be overdilated, or elongation along the axis may cause a normal body cavity or blood vessel to be dilated.

Nylons or polyamides have substantially intermediate properties between polyethylene terephthalate and polyolefins. If they are formed to be thinned, characteristics with respect to the pressure capacity and pinholes may be undesirable. If formed to be thick, the resulting balloon can become hard and may not have satisfactory trackability.

Techniques of forming a balloon by laminating a plurality of materials in the form of layers are disclosed, for example, in Japanese Patent Laid-open No. Hei 3-205064 and Japanese Patent Laid-open No. Hei 9-164191.

In Japanese Patent Laid-open No. Hei 3-205064, there is proposed a technique wherein a multi-layered balloon including a layer containing polyethylene terephthalate and a layer containing a polyolefin is described. A hydrophilic polymer may be coated on an outer surface of the balloon. It is stated that such a balloon is consequently excellent in lubricity, breaking strength, limited radial expansion, bondability with a shaft, and reinforcing characteristics including rupture characteristics.

In Japanese Patent Laid-open No. Hei 9-164191, there is described a balloon of a multi-layered structure having a base layer made of a high-strength polymer, and a covering layer formed on at least one surface of the base layer and made of a flexible polymer that is more flexible than the high-strength polymer. It is disclosed that the flexible polymer can have an elongation at breakage close to the high-strength polymer and be more flexible than the high-strength polymer. It is disclosed that when a high-strength polymer and a flexible polymer that has an elongation at breakage close to that of the high-strength polymer and is more flexible than the high-strength polymer are thus chosen to provide a multi-layered balloon, the flexible polymer fully functions to improve the strength of the balloon as a whole to obtain a flexible balloon of high strength. It is stated that such a balloon can be formed thicker than a balloon made of a single high-strength polymer layer, so that pinholes are reduced.

SUMMARY

In Japanese Patent Laid-open No. Hei 3-205064 and Japanese Patent Laid-open No. Hei 9-164191, it is attempted to address exemplary problems associated with the flexibility, thinning capability and high strength desired for catheter balloons by providing a balloon having a multi-layered structure formed by laminating layers made of different types of materials. However, the balloon for catheter obtained by laminating layers of different types of materials can have a problem in mutual adhesion (or bonding) of the layers. For example, if the mutual adhesion force of the layers is low, interfacial separation takes place and in some cases, there can be a concern that the balloon is broken in a body cavity or blood vessel. For example, at paragraph number [0025] of the Japanese Patent Laid-open No. Hei 9-164191, it is stated that when a ratio between the elongation at breakage of the high-strength polymer and the elongation at breakage of the flexible polymer is set at 1:0.7 to 1:1.3, the elongations of the layer made of the high-strength polymer and the layer made of the flexible polymer come close to each other in case where the resulting balloon is inflated such as by application of pressure, for which no separation between the layers occurs as can be caused because one of the layers is stretched too far to permit the other layer to follow.

For example, in the Japanese Patent Laid-open No. Hei 9-164191, the difference between the elongations at breakage of the respective layers is set within a certain range so as to prevent the degradation as will be caused by the change in physical properties, such as inflation and deflation, of the balloon. As a consequence, the separation between the layers, which can be caused for the reason that one of the layers elongates too far to permit the other layer to follow, is suppressed or prevented independently of the adhesion force therebetween.

However, the cause of degradation such as the mutual interfacial separation between the layers made of different types of materials can be attributed not only to the degradation ascribed to the change occurring as a result of the dynamic action such as of the inflation and deflation of the balloon, but also to the static degradation that proceeds in association with a complicated action such as of sterilization and disinfection of the balloon, the hydrolysis and oxidative decomposition caused by a number of environmental factors inside a living body and the like. Accordingly, in order to deal not only with the dynamic degradation, but also with the static degradation, it can be desirable to improve the mutual adhesion of the layers at the molecular level. According to an exemplary aspect, a balloon for catheter is provided wherein the adhesion per se between different types of layers is improved.

According to an exemplary aspect, a balloon for catheter is provided, which includes a film body having a flexible covering layer containing a polyamide elastomer having specific physical properties.

According to an exemplary aspect, there can be provided a balloon for catheter, which is excellent in adhesion between layers made of different types of materials. An exemplary balloon for catheter has a layer containing a polyamide elastomer and is thus flexible and excellent in capability of passage through a blood vessel or body cavity. In addition, an exemplary balloon is provided with the hard layer containing a polyamide and has thus a satisfactory pressure resistance.

According to an exemplary aspect, a balloon for a catheter is provided, comprising: a film body that is inflatable and deflatable by a fluid supplied from a catheter, wherein said film body includes a hard layer containing a polyamide and a flexible layer formed on the hard layer and containing a polyamide elastomer having a Shore D hardness that is not larger than 62, and a content of amide units of the polyamide elastomer in the flexible layer is not less than 60 wt %.

According to an exemplary aspect, a balloon catheter is provided, comprising: an inner tube having a first lumen opened at a distal end thereof; an outer tube coaxially provided with said inner tube, having a distal end distanced from the distal end of said inner tube toward a proximal end at a given length, and having a second lumen between the outer surface of said inner tube and the outer tube; a hub having an opening communicating with said second lumen; and a balloon fixed to said inner tube at a distal end thereof, fixed to said outer tube at a proximal end thereof, and communicating in the inside thereof with said second lumen, wherein a fluid is charged or discharged from said opening to inflate or deflate said balloon, wherein the balloon comprises a film body, wherein said film body includes a hard layer containing a polyamide and a flexible layer formed on the hard layer and containing a polyamide elastomer having a Shore D hardness that is not larger than 62, and a content of amide units of the polyamide elastomer in the flexible layer is not less than 60 wt %.

DETAILED DESCRIPTION

According to an exemplary embodiment, there is provided a balloon for catheter of the type having a film body that is inflatable and deflatable by means of a fluid supplied from a catheter. The film body can include a hard layer containing a polyamide and a flexible layer formed on the hard layer and containing a polyamide elastomer whose Shore D hardness is not larger than 62 and that the content of the amide units of the polyamide elastomer in the flexible layer is not less than 60 wt %.

A balloon for catheter can be provided, for example, which is excellent in the adhesion between the layers made of different types of materials.

Figure 1A:
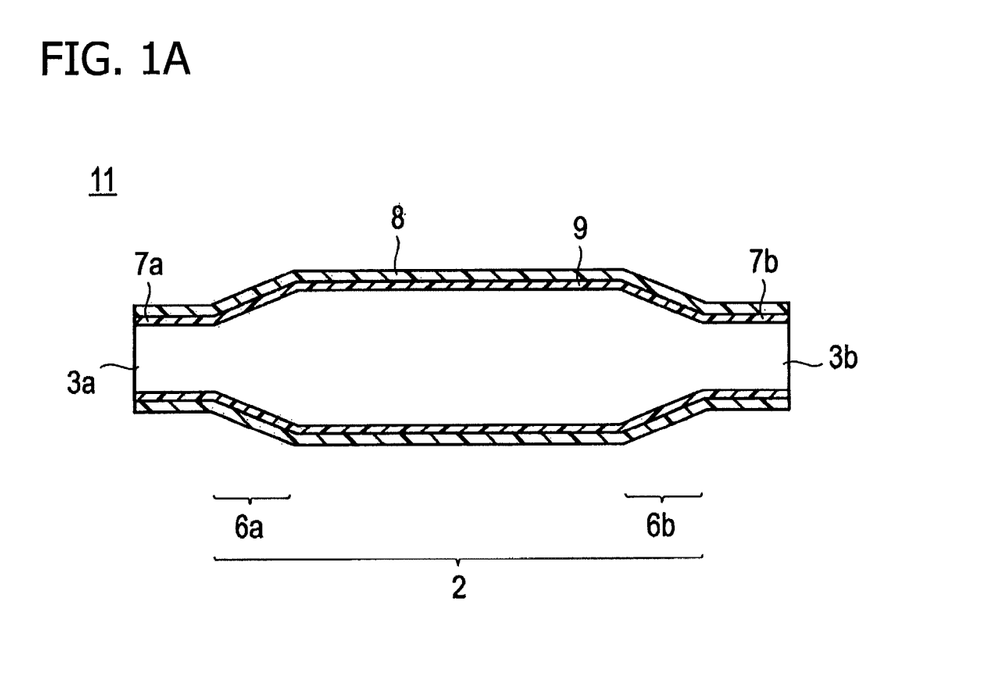
FIG. 1A is a schematic view showing an example of a balloon for catheter according to an exemplary aspect.
Figure 1B:
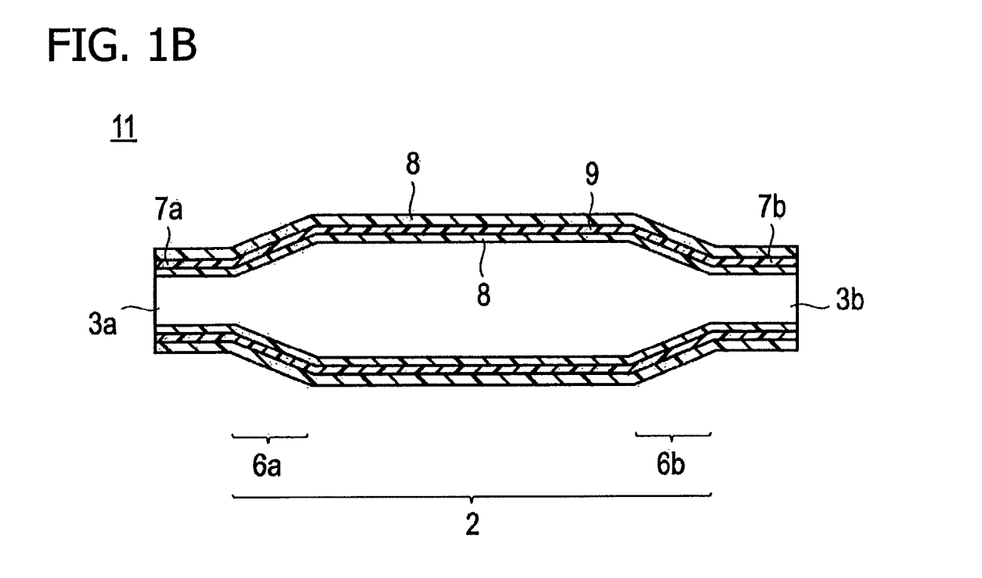
FIG. 1B is a schematic view showing another example of a balloon for catheter according to an exemplary aspect.

The balloon has no specific limitation thereon, and a balloon shaped in any suitable form may be used. The structure of the balloon is illustrated with reference to the accompanying drawings. FIGS. 1A and 1B, respectively, show an example of a balloon for catheter. FIG. 1A is a sectional view of an example of a double-layered structure of a balloon for catheter including a hard layer and the flexible layer. FIG. 1B is a sectional view of an example of a three-layered structure of a balloon for catheter including a flexible layer-hard layer-flexible layer structure.

An exemplary balloon 11 for catheter can be composed of a tubular film body 2 that is inflatable or deflatable by the action of a fluid to be supplied from a catheter, and connection portions 7a and 7b extending from axially opposite ends of the film body and connected to the catheter. The connection portions 7a and 7b at the opposite ends can be formed with openings 3a and 3b inserted from the catheter, respectively. The opening 3b at one of the connection portions can be formed to have a diameter larger than the opening 3a at the other connection portion. The balloon 11 can have a tubular portion having a substantially uniform outer diameter for permitting dilation of a stenosis of a lumen in the body such as a blood vessel, a urinary duct, a billary duct or the like.

The size of the balloon for catheter can be such that an outer diameter of the tubular film body in inflated state is 1.0 to 35.0 mm, for example, 1.5 to 30.0 mm. The length of the tubular film body along the major axis can be 3.0 to 80.0 mm, for example, 10.0 to 75.0 mm. The total length (i.e., a total length of the tubular film body and the connection portions along the major axis) of the balloon can be 5.0 to 120.0 mm, for example, 15.0 to 100.0 mm.

The cross-sectional shape of the tubular film body is not specifically limited and may include, for example, a circular, ellipsoidal, substantially ellipsoidal or polygonal form. The shapes of the opposite ends of the tubular film body may, respectively, be tapered as is shown in FIGS. 1A and 1B. The balloon can include the cylindrical film body having opposite ends provided with tapered portions 6a and 6b, and the connection portions 7a and 7b extending outwardly of the axis and connected with a catheter and contiguous with the tapered portions 6a and 6b, respectively. In addition, the opposite connection portions can be formed with the openings 3a and 3b inserted from the catheter, respectively.

Where the tubular film body is tapered at the opposite ends thereof, the central portion of the tubular film body can be a portion that keeps the largest diameter of the balloon therethrough, and the tapered portions 6a and 6b can be portions, which are contiguous with the central portion of the tubular film body and of which diameter is so changed as to be continuously reduced toward the end.

The connection portions 7a and 7b connecting with the catheter can be contiguous with the tapered portions 6a and 6b, respectively, and can become small diameter portions having substantially the same inner diameter, at which the balloon is attached with the catheter and the openings 3a and 3b are formed, respectively. The tapered portions 6a and 6b and the connection portions 7a and 7b with the catheter can be provided at opposite sides of the tubular film body of the balloon, respectively, and the respective tapered portions and the respective connection portions may differ in shape from each other.

The film body can be formed of a laminated film of a plurality of layers. For example, the film body can be formed of a film wherein at least two layers are laminated including a polyamide elastomer-containing flexible layer laminated on the surface of a polyamide-containing layer. For example, the hard layer and the flexible layer can be, respectively, made of a film laminated with two to five layers and, for example, the film body can be formed of a film wherein three layers in total of the hard and flexible layers are laminated. The order of lamination of the polyamide-containing hard layer and the polyamide elastomer-containing flexible layer can be varied. For example, the flexible layer containing a polyamide elastomer can be formed as an outermost layer at the inner side and as an outermost layer at the outer side, respectively. For example, mention is made of a three layer structure including polyamide elastomer-containing flexible layer/polyamide-containing hard layer/polyamide elastomer-containing flexible layer.

In an exemplary embodiment, when the polyamide elastomer-containing flexible layer is formed as the outermost layer, it becomes possible to improve abrasion resistance, protect the strength layer from damage from outside, and reduce or prevent pinholes.

If desired, a biocompatible material or antithrombotic material may be further covered on the surface of the polyamide elastomer-containing layer serving as an outermost layer to be contacted with a living body. As such a biocompatible or antithrombotic material, there may be used a number of suitable polymers singly or in admixture. For example, there can be conveniently used natural polymers such as collagen, gelatin, chitin, chitosan, cellulose, polyaspartic acid, polyglutamic acid, polylysine, casein and the like, and synthetic polymers such as phospholipid polymer, a block polymer of MPC (methacryloyloxyethylphosphorylcholine) having a phosphoric group at the side chain, polyhydroxyethyl methacrylate, a copolymer of hydroxyethyl methacrylate and styrene (e.g. hydroxyethyl methacrylate-styrene-hydroxyethyl methacrylate block copolymer), polymethyl methacrylate, polylactic acid, polyglycolic acid, lactic acid-glycolic acid copolymer, polyethylene, polypropylene and the like.

In order to permit easy insertion of the balloon into a blood vessel or further into a guide catheter, the balloon or the outer surface of the film body can be treated for the purpose of ensuring lubricity when in contact with blood. Such a treatment can include, for example, surface coating or surface fixing of a hydrophilic resin such as poly(2-hydroxyethyl methacrylate), polyhydroxyethyl acrylate, hydroxypropyl cellulose, methyl vinyl ether/maleic anhydride copolymer, polyethylene glycol, polyacrylamide, polyvinylpyrrolidone, dimethylacrylamide/glycidyl methacrylate random or block copolymer or the like.

For example, the polyamide elastomer-containing flexible layer can be formed in intimate contact with the surface of the polyamide-containing hard layer. For example, the flexible layer can be formed in intimate contact with the entire surface of the hard layer.

There can be provided a balloon for catheter wherein adhesion per se of the different types of layers is improved.

The tubular film body can have an average thickness of 5 to 50 μm, for example, 10 to 30 μm, under deflated conditions.

For example, the average thickness of the film body under deflated conditions within a range of 10 to 30 μm can be favorable from the standpoint of trackability and the capability of passage through a stenosis of a blood vessel or a stenosis such as of a body cavity.

The average thickness of the polyamide elastomer-containing flexible layer of the film body can be 0.5 to 10 μm, for example, 1 to 5 μm.

The average thickness of the polyamide-containing hard layer of the film body can be 0.5 to 49.5 μm, for example, 5 to 25 μm.

The tubular film body can be formed of a film made of a laminate of a plurality of layers. The connection portions, which can be formed at opposite ends of the film body and are to be connected with a catheter, may be ones integrated with the film body (integrally molded ones), or may be ones bonded with a separate, substantially cylindrical film body whose diameter is smaller than the tubular film body. The average thickness of the connection portions in a normal condition can be 5 to 50 μm, for example, 10 to 30 μm.

The balloon for catheter can be provided with the film body, which is capable of being inflated or deflated by the action of a fluid supplied from a catheter, and thus can be foldable. For example, in a deflated condition, the balloon can be folded about the outer periphery of a body tube of the catheter. The material for the film body that enables the balloon to be inflatable or deflatable can include an elastomer.

As the fluid supplied from the catheter, mention is made of suitable ones including a contrast agent, helium gas, physiological saline solution, $CO_2$ gas, $O_2$ gas, $N_2$ gas, air and the like.

The hard layer 9 can contain a polyamide and may further contain suitable additives and a contrast agent for X-rays, if desired, or may be made only of the polyamide. For example, in the hard layer, if the polyamide is present in an amount of 60 to 100 wt %, a pressure capacity desirable for the balloon for catheter can be secured.

The polyamide can be a polymer having an acid amide bond (—CO—NH—) in the main chain. For example, the polyamide can be prepared by polymerizing a lactam or amino acid of a ring structure or by condensation polymerization of a dicarboxylic acid and a diamine. Accordingly, the polyamide used can be a homopolyamide. Monomers that are polymerizable by themselves include e-caprolactam, aminocaproic acid, enantholactam, 7-amino-heptanoic acid, 11-amino-undecanoic acid, 12 amino-dodecanoic acid, 9-aminononanoic acid, piperidone and the like.

The dicarboxylic acid that can be used for the condensation polymerization between the dicarboxylic acid and the diamine includes adipic acid, sebacic acid, dodecanedicarboxylic acid, glutaric acid, terephthalic acid, 2-methylterephthalic acid, isophthalic acid, naphthalene dicarboxylic acid and the like. The diamines include tetraethylenediamine, hexamethylenediamine, nonamethylenediamine, decamethylenediamine, undecamethylenediamine, dodecamethylenediamine, paraphenylenediamine, metaphenylenediamine and the like.

The polyamide can include nylons 4, 6, 7, 8, 11, 12, 6.6, 6.9, 6.10, 6.11, 6.12, 6T, 6/6.6, 6/12, 6/6T, 6T/6I and the like. It will be noted that the polyamide used in the examples is nylon 12.

The polyamide may be blocked with a carboxylic acid, an amine or the like at the terminal ends thereof. The carboxylic acid can include an aliphatic monocarboxylic acid such as adipic acid, caproic acid, caprylic acid, capric acid, lauric acid, myristic acid, palmitic acid, stearic acid, behenic acid or the like. The amine can include an aliphatic primary amine such as hexylamine, octylamine, decylamine, laurylamine, myristylamine, palmitylamine, stearylamine, behenylamine or the like. The polyamide resins may be used singly or in combination of two or more. Of those polyamides indicated above, nylon 12 can be used as a polyamide.

The weight-average molecular weight of the polyamide can be within a range of $2.0 \cdot 10^4$ to $5.0 \cdot 10^4$, for example, $3.0 \cdot 10^4$ to $5.0 \cdot 10^4$, for example, $4.0 \cdot 10^4$ to $5.0 \cdot 10^4$.

It will be noted that the molecular weight of the polymer can be measured according to any suitable method including an MS spectra method, a light scattering method, liquid chromatography, gas chromatography, gel permeation chromatography (GPC) and the like. For example, the molecular weight can be measured according to GPC.

The contrast agent such as for X-rays can be radiopaque, and suitable radiopaque materials can be used. For example, mention is made of iodine, barium, bismuth, boron, bromine, calcium, gold, platinum, silver, iron, manganese, nickel, gadolinium, dysprosium, tungsten, tantalum, stainless steel, nitinol and compounds thereof such as barium sulfate, and solutions/dispersions thereof (e.g., physiological saline solution); amidotrizoic acid or 3,5-diacetamino-2,4,6-triiodobenzoic acid, meglumine sodium amidotrizoate, meglumine amidotrizoate, sodium iotalamate, meglumine iotalamate, meglumine iotroxate, iotrolan, ioxaglic acid, ioxilan, Iopamidol, iopromide, iohexol, ioversol and iomeprol; and ethyl esters of iodized poppy seed fatty acid (e.g., Lipiodol™, which is a poppy seed oil whose carbon atoms are iodized). These radiopaque materials may be used singly or in admixture of two or more. A contrast agent layer making use, as a base, of such a contrast agent as indicated above may be further laminated on the film body.

This can allow the degree of inflation of the balloon to be confirmed under radiographic guidance, ensuring reliable and easy confirmation of the balloon position.

The flexible layer 8 contains a polyamide elastomer and may further include suitable additives and a contrast agent such as for X-rays, if desired, or may be formed of at least one polyamide elastomer. The polyamide elastomers may be used singly or in combination of two or more. For example, if the polyamide elastomer is contained in an amount of 60 to 100 wt % in the flexible layer, there can be secured trackability, the capability of passage through a stenosis such as of a blood vessel, both of which can be desirable for a balloon for catheter, and flexibility desirable for inflating a stenosis such as of a calcified blood vessel.

The polyamide elastomer can have a Shore D hardness of not larger than 62, and the content of the amide units in the polyamide elastomer can be not less than 60 wt %.

The sentence "the content of the amide units in the polyamide elastomer is not less than 60 wt %" means that the content of the amide units (which is called repeating units derived from the amide bond) in the polymer chain of the polyamide elastomer is not less than 60 wt % based on the weight of the whole polyamide elastomer.

For example, from the standpoint of trackability, the capability of passage through a stenosis such as of a blood vessel or body cavity and the pressure resistance, the polyamide elastomer can have a Shore D hardness of not larger than 62 and the content of the amide units in the polyamide elastomer can be not less than 60 wt %.

For example, the polyamide elastomer can have a Shore D hardness of from 50 to 65 and the content of the amide units in the polyamide elastomer can be from 60 wt % to 90 wt %. For example, the Shore D hardness ranges from 54 to 62, and the content of the amide units in the polyamide elastomer ranges from 60 wt % to 85 wt %.

The Shore D hardness ranging 54 to 62 and the content of the amide units in the polyamide elastomer ranging from 60 wt % to 85 wt % are exemplary in view of the trackability, the capability of passage through a stenosis such as of a blood vessel or body cavity and the pressure resistance.

For the measurement of the hardness of a polyamide elastomer, there can be used a Shore D hardness accorded to ISO 868.

For the calculation of the content of the amide units in the polyamide elastomer, $^1$H-NMR and $^{13}$C-NMR can be used to specify an amide unit-derived peak in the polyamide elastomer. The unit ratio of the amide units in a single polymer chain can be calculated from the integral ratio of $^1$H-NMR, which is subsequently multiplied by the molecular weight of the amide unit to provide the resulting value as wt % of the amide units.

For example, in a case where the flexible layer contains two or more kinds of polyamide elastomers, the respective amide-derived peaks are specified and the unit ratios derived from the respective amide units are calculated from the integral ratios of $^1$H-NMR in the same manner as set out above to determine the weight percent of the amide units in the case containing two or more kinds of polyamide elastomers.

The terms "amide units in the polyamide elastomer" used herein mean repeating units derived from amide bonds in the polymer chain of the polyamide elastomer. The amide units in the polyamide elastomer can be at least one of the repeated units represented by the following formulas (1) and (2):

wherein n is, for example, an integer of 5 to 11; and wherein a is, for example, an integer of 4 to 12, for example, 11 or 12, and b is, for example, an integer of 4 to 10, for example, 4 to 8.

Thus, the polyamide elastomer can contain at least either of the repeating units represented by the above formula (1) or (2).

When the flexible layer containing a polyamide elastomer having such amide units is formed on the polyamide-containing hard layer, the amide unit moieties of the polyamide elastomer and the polymer chains of the polyamide can be strongly bonded together by the mutual interaction thereof. When the flexible layer containing the polyamide elastomer having the amide units and the polyamide-containing hard layer are subjected to thermocompression bonding, the amide unit moieties of the polyamide elastomer and the polymer chains of the polyamide can be rendered fluid thereby further improving thermal adhesion.

The polyamide elastomer can be made of a polyamide block copolymer, for example, a two-dimensional block copolymer. The polyamide block copolymer can contain not less than 60 wt % of the amide units of the formula (1) or (2) relative to the weight (100 wt %) of a single polymer chain of the polyamide block copolymer, and the Shore D hardness of the polyamide block copolymer can be not larger than 62.

For example, the polyamide block copolymer can contain at least one selected from the group consisting of the copolymers of the following formulas (3) and (4):

wherein a is an integer of 4 to 12, b is an integer of 4 to 10, c and d are, respectively, an integer of 0 to 100, p is an integer of 2 to 4, q is an integer of 1 to 100, and Ln is a linker moiety and represents —C(O)—R—C(O)— wherein R represents an alkylene group having 2 to 12 methylene units, for example, an alkylene group having 4 to 10 methylene units; and wherein n is an integer of 5 to 11, m and l are, respectively, an integer of 0 to 100, p is an integer of 2 to 4, q is an integer of 1 to 100, and Ln is a linker moiety and represents —C(O)—R—C(O)— wherein R represents an alkylene group having 2 to 12 methylene units, for example, an alkylene group having 4 to 10 methylene units.

In the above formulas, the alkylene group having 2 to 12 methylene units represented as R may be linear, branched or cyclic. For example, mention is made of a tetramethylene group, a 2-methylpropylene group, a 1,1-dimethylethylene group, an n-pentylene group, an n-hexylene group, an n-nonylene group, a 1-methyloctylene group, a 6-methyloctylene group, a 1-ethylheptylene group, a 1-(n-butyl)pentylene group, a 4-methyl-1-(n-propyl)pentylene group, a 1,5,5-trimethylhexylene group, a 1,1,5-trimethylhexylene group, an n-decylene group, a 1-methylnonylene group, a 1-ethyloctylene group, a 1-(n-butyl)hexylene group, a 1,1-dimethyloctylene group, a 3,7-dimethyloctylene group, an n-undecylene group, a 1-methyldecylene group and the like.

The flexible layer may be formed by use of the polyamide block copolymers of the formulas (3) and (4) singly or in combination of two or more. Where two or more of the polyamide block copolymers of the formulas (3) and (4) are used in combination as the flexible layer, they can be so mixed that the content of the amide units in the polyamide elastomer is set at not less than 60 wt % as a whole of the flexible layer and the Shore D hardness is not larger than 62.

The polyamide elastomer may be a synthetic one or a commercially available one. Suitable polyamide elastomers include ELG5660 (made by EMS Inc., with a commercial name of Grilflex having a polyamide block ratio of 67 wt % and a Shore D hardness of 56), ELG 6260 (made by EMS Inc., with a commercial name of Grilflex having a polyamide block ratio of 85 wt % and a Shore D hardness of 62) or the like.

The weight-average molecular weight of the polyamide elastomer can be $1.0 \cdot 10^4$ to $1.0 \cdot 10^5$, for example, $2.0 \cdot 10^4$ to $5.0 \cdot 10^4$, for example, $2.0 \cdot 10^4$ to $4.0 \cdot 10^4$. The molecular weight of the polyamide elastomer can be measured in the same manner as that of the polyamide.

The polyamide block copolymer may be blocked with a carboxylic acid, an amine or the like at terminal ends thereof. As the carboxylic acid, mention is made of aliphatic monocarboxylic acids such as adipic acid, caproic acid, caprylic acid, capric acid, lauric acid, myristic acid, palmitic acid, stearic acid, behenic acid and the like. The amine can include an aliphatic primary amine such as hexylamine, octylamine, decylamine, laurylamine, myristylamine, palmitylamine, stearylamine, behenylamine or the like.

The contrast agent such as for X-rays, which may be contained in the flexible layer, may be the same as the contrast agent described with respect to the hard layer.

An exemplary embodiment of the balloon materials for catheter includes a polyamide-containing hard layer and a polyamide elastomer-containing flexible layer laminated in intimate contact with the hard layer at opposite surfaces thereof (for example, both the inner and outer surfaces thereof) wherein the polyamide is made of at least one selected from the group consisting of nylon 11, nylon 12 and nylon 6.12 and the polyamide elastomer is made of at least one selected the group consisting of those polymers of the foregoing formulas (3) and (4).

For example, the combination of the polyamide-containing hard layer and the polyamide elastomer-containing flexible layer can contribute to improved thermal adhesion, so that there can be formed a balloon that is excellent in flexibility and thinning capability along with excellent interlayer adhesion and is high in strength.

Method for Making a Balloon for Catheter

An exemplary embodiment of a method for making a balloon for catheter is now described. The method for making a balloon can include: (1) forming a double-molded (double-layered) or triple-molded (three-layered) polymer tube (parison) obtained by thermocompression of such a polyamide-containing layer as set out hereinbefore and a polyamide block polymer-containing layer or layers having given characteristics as set out before; (2) axially stretching the parison at a temperature within a range of the secondary transition temperatures to the primary transition temperatures of both polymers and further biaxially stretching the stretched parison by radial inflation; (3) cooling the inflated parison down to the secondary transition temperatures of both polymer and deflating the thus cooled parison to form a biaxially stretched balloon having a tubular film body having a substantially uniform inner diameter, a tapered portion provided at opposite sides of the film body, respectively, and a connection portion with a catheter provided at each tapered portion, and (4), if desired, re-stretching the tapered portion of the biaxially stretched balloon so that the tapered portion is thinned, inflating the re-stretched balloon, heating the balloon to not lower than the secondary transition temperatures of the polymers while keeping the inflated state, and cooling the balloon to a temperature not higher than the secondary transition temperatures of the polymers.

The respective exemplary steps are now illustrated.

(Step 1)

Figure 2:
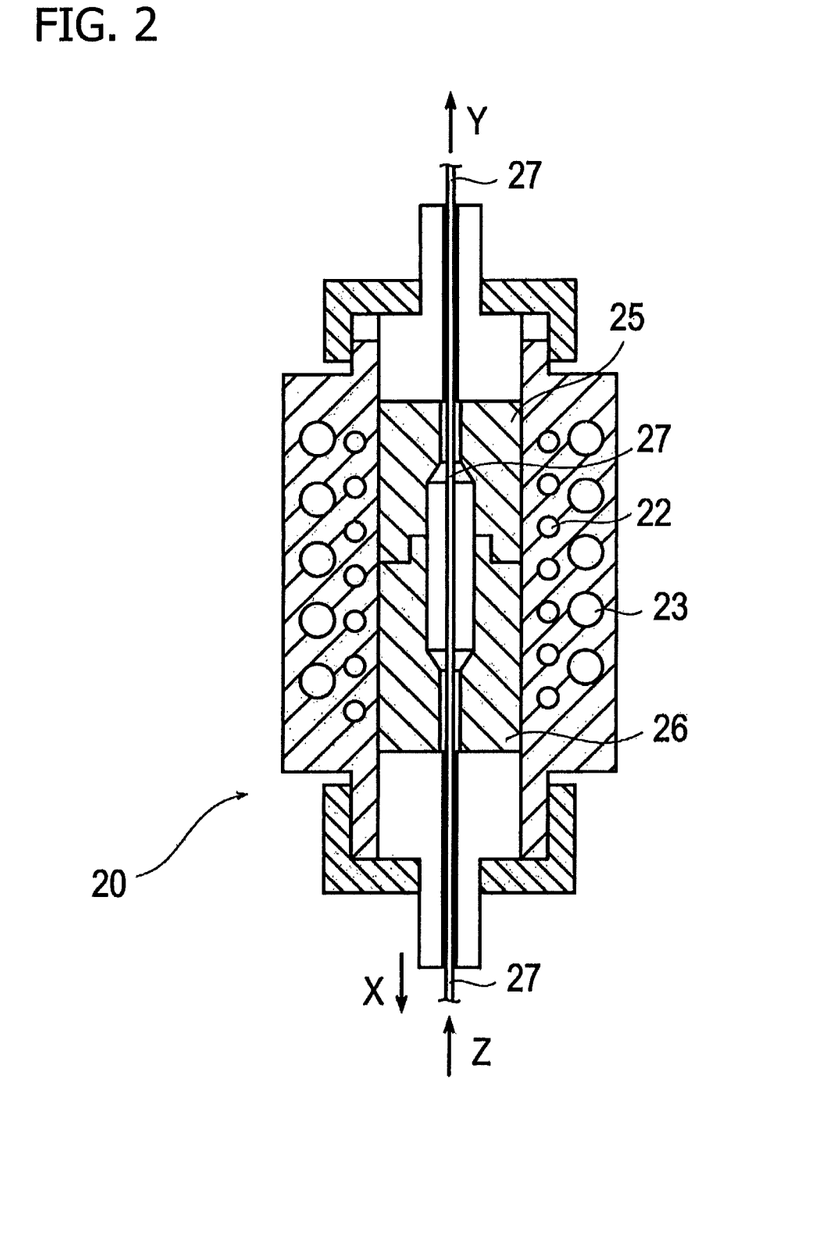
FIG. 2 is a schematic illustrative view showing a mold for a balloon for catheter according to an exemplary aspect.

The step 1 of forming a tubular parison from stretchable polymers can include subjecting a film made of a polyamide and a film or films made of a polyamide elastomer to thermocompression to form a film made of at least two layers, for example, three layers including the polyamide film and the polyamide elastomer film formed on opposite surfaces of the polyamide film by thermocompression, and forming a tube 27 made of two or more types of polymers as shown in FIG. 2. This can be carried out according to a wire coating method making use of double (double-layer) or triple (three-layer) extrusion. For example, there may be used a method wherein a tube made of a polymer for forming a hard layer or flexible layer has been preliminarily formed, on which a polymer forming other layer or layers is coated. The polymers used may be ones set forth hereinbefore.

(Step 2)

The tube 27 can be inserted into a mold 20 shown in FIG. 2 and, for example, is blocked at one end thereof. The blocking method can be carried out by use of heat sealing, sealing with a high frequency, a clamp or the like. FIG. 2 is a sectional view of the balloon mold 20. The mold 20 has a heater 22 for use as heating means and a cooling pipe 23 for cooling means. An inner shape of separate molds 25 and 26 in a combined state corresponds to a fundamental outer shape of a balloon to be formed.

As shown in FIG. 2, the heater 22 can be started so that the tube 27 at a portion thereof where a balloon 11 is to be formed is heated to a temperature within a range of from the secondary transition temperatures of the polymers to the primary transition temperatures, for example, to a temperature slightly exceeding the secondary transition temperatures. While keeping the tube 27 in the heated condition, the tube 27 can be stretched toward the directions of arrows X and Y and a gas can be fed from the direction of arrow Z into the tube 27 under pressure, thereby causing the tube 27 at the portion thereof where heated within the mold 20 to be brought into intimate contact with the inner wall surfaces of the separate molds 25 and 26.

(Step 3)

A liquid coolant can be circulated through the cooling pipe 23 to cool the tube 27 down to a level not higher than the secondary transition temperatures. This cooling may be performed, for example, merely by allowing to stand for natural cooling without circulation of a liquid coolant. Thereafter, the tube 27 can be returned to a normal pressure at the inside thereof and removed from the mold 20. The tube 27 can be subsequently cut off at a tip and rear end portions thereof to provide a fundamental shape of balloon as shown in FIGS. 1A and 1B. The balloon having an intended thickness may be formed by repeating the above stretching operations twice.

(Step 4)

The tapered portions 6a and 6b of the biaxially stretched balloon may to re-stretched so that the tapered portions are rendered thinner. A re-stretching tool may be used so as to re-stretch the tapered portions 6a and 6b or both the tapered portions 6a and 6b and the connection portions 7a and 7b with catheter. The re-stretching tool can have two balloon-fixing chucks, and the fixing chuck can be movably attached to a support base and can be so configured as to be moved back and forth by rotation of a handle.

A balloon catheter is now described according to an exemplary embodiment. It will be noted that like elements are indicated by like reference numerals in the drawings and are not repeatedly illustrated. The dimensions in the drawings are not necessarily to scale and are for illustrative convenience, and may thus differ from actual dimensions.

[Balloon Catheter]

Figure 3:
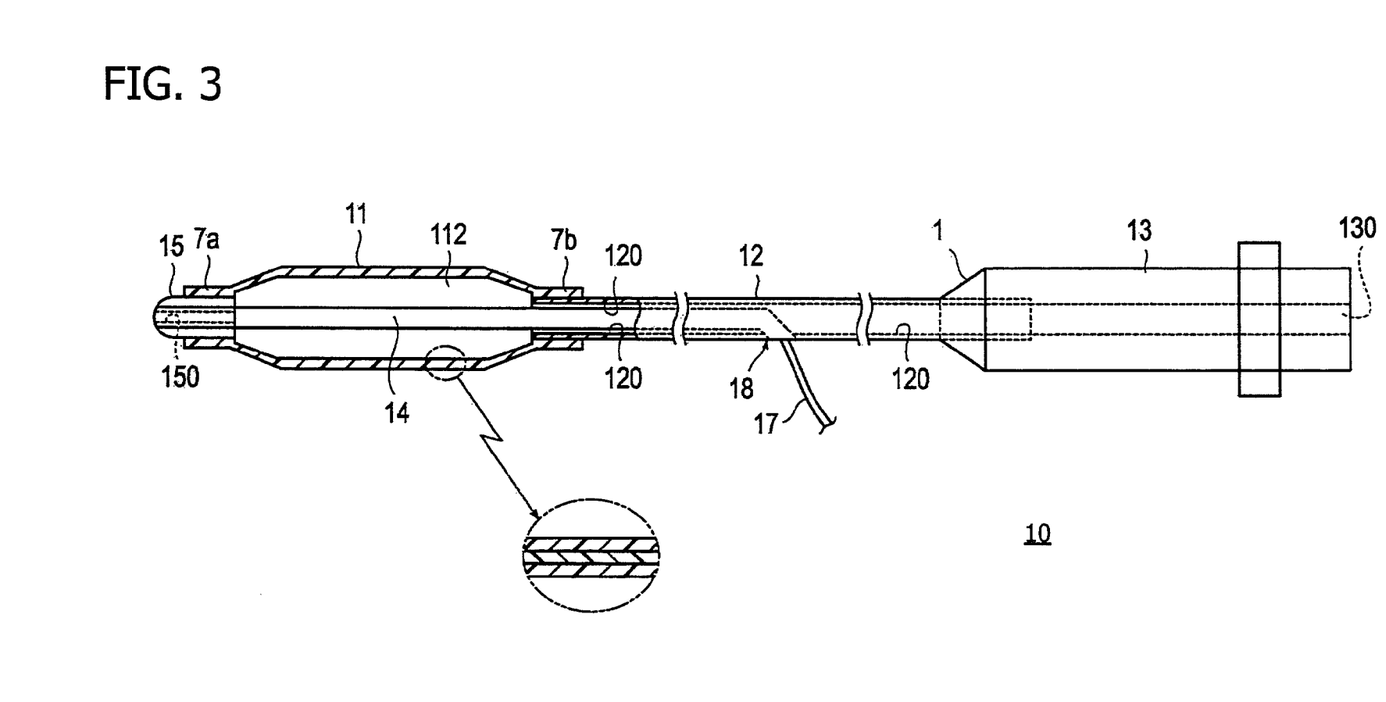
FIG. 3 is a schematic view showing an example of a balloon catheter according to an exemplary aspect.

An exemplary balloon catheter is illustrated with reference to the drawing. FIG. 3 is an external view showing an exemplary balloon catheter for dilatation of a blood vessel.

As shown in FIG. 3, a balloon catheter 10 can have a catheter body 1 provided with an elongated outer tube 12 capable of transferring a fluid, a balloon 11 connected at the distal end of the catheter body 1, and a hub 13 attached at the proximal end of the catheter body 1. The balloon catheter 10 also can have an inner tube 14 passing through a lumen 120 formed inside the outer tube 12, and a distal end member 15 provided at the distal end of the inner tube 14. The distal end means an end portion located at a side of insertion into the vessel when in use. The proximal end means an end portion located at a side of an operator handling the balloon catheter when in use.

In FIG. 3, for example, there is shown an instance of a rapid exchange type catheter wherein the catheter is in the form of coaxial double lumen at the proximal end thereof and is provided with a wire port between the distal end and the proximal end, through which a guide wire can be inserted. The balloon may also be applied to an over-the-wire catheter.

The balloon catheter 10 can be applied as a catheter for dilatation of a blood vessel. The balloon and balloon catheter may also be applicable to other types of catheters such as a urethral catheter and the like.

An exemplary structure of the balloon catheter 10 is described in more detail. As shown in FIG. 3, the balloon catheter 10 can include the inner tube 14 having a first lumen 150 (an outer lumen at the inside) with its distal end being opened, an outer tube 12 that is coaxially provided with the inner tube 14 at a position disposed from the distal end of the inner tube 14 toward the proximal end by a given distance and forms a second lumen 120 with the outer surface of the inner tube 14. The balloon catheter 10 can include a connection portion (at the distal end of the balloon) 7a with the catheter and a connection portion (at the proximal end of the balloon) 7b with the catheter wherein the connection portion 7b is attached to the outer tube 12 and the connection portion 7a is attached to the inner tube 14. The balloon catheter 10 can include a foldable balloon 11 communicating with the second lumen 120 in the vicinity of the proximal end, and a hub 13 provided with an opening 130 communicating with the second lumen.

The balloon catheter 10 can include a catheter body 1 having an inner tube 14 and an outer tube 12, a hub 13 and a balloon 11. The inner tube 14 can have a first lumen 150 (an outer lumen at an inner side) opened at its distal end. The first lumen 150 can be one for inserting a guide wire therethrough. Because a wire port 18 that is a first opening 18 serving as a guide wire port and the first lumen 150 can communicate with each other, a guide wire 17 can be inserted therethrough. The opening 18 forming the guide wire port can be attached to an intermediate portion of the outer tube 12. An opening 130 communicating with the second lumen 120 can communicate with a balloon inside 112 through the second lumen 120, so that charge/discharge of a fluid from the opening 130 enables the balloon to be inflated/deflated.

The inner tube 14 can have an outer diameter of 0.3 to 2.5 mm, for example, 0.4 to 2.0 mm and an inner diameter of 0.2 to 2.35 mm, for example, 0.25 to 1.7 mm. The material for the inner tube 14 can be one that has flexibility to some extent and can include, for example, a polyolefin such as polyethylene, polypropylene, ethylene-propylene copolymer, ethylene-vinyl acetate copolymer or the like, or a thermoplastic resin such as polyvinyl chloride, polyurethane, polyamide, polyamide elastomer, polyester elastomer or the like.

The outer tube 12 has the inner tube 14 inserted therethrough and is provided at a position slightly disposed from the distal end of the inner tube at the distal end thereof, and the second lumen 120 is formed between the inner surface of the outer tube 12 and the outer surface of the inner tube 14. Accordingly, there can be provided a lumen having a satisfactory capacity. The second lumen 120 can be communicated with at the distal end thereof inside of the balloon 11 at the rear end thereof and can in turn be communicated with at the rear end thereof to the second opening 130 of the hub 13 forming an injection port for charging a fluid (e.g., a contrast agent, helium gas, physiological saline solution, $CO_2$ gas, $O_2$ gas or the like) for balloon inflation. The outer tube 12 can have an outer diameter of 0.5 to 4.3 mm, for example, 0.6 to 4.0 mm, and an inner diameter of 0.4 to 3.8 mm, for example, 0.5 mm to 3.0 mm.

If desired, a contrast agent such as for X-rays or the like may be charged into the balloon when the balloon is inflated.

The material for the outer tube 12 can have flexibility to some extent and can include, for example, a polyolefin such as polyethylene, polypropylene, ethylene-propylene copolymer, ethylene-vinyl acetate copolymer or the like, or a thermoplastic resin such as polyvinyl chloride, polyurethane, polyamide, polyamide elastomer, polyester elastomer or the like.

In FIG. 3, the balloon catheter 10 can have, at the distal end thereof, a spherical distal end member 15 for the purposes not only of playing a role of helping blood vessel tracking, but also of not damaging the vessel walls.

The balloon 11 can be foldable and can be folded about the outer periphery of the inner tube 114 in a deflated state. The balloon 11 can be a foldable one that has a tubular body of substantially uniform diameter, at least a part of which is cylindrical so as to easily dilate a stenosis of a blood vessel or body cavity. The balloon 11 can be configured such that the connection portion 7b is liquid-tightly fixed to the distal end portion of the outer tube 12 by means of a bonding agent or by thermal fusion bonding. For example, the connection portion 7a can be liquid-tightly fixed to the distal end portion of the inner tube 14 by means of a bonding agent or by thermal fusion bonding.

As shown in FIG. 3, the balloon 11 can have an expanded space 112 formed between the inner surface of the balloon 11 and the outer surface of the inner tube 14. This expanded space 112 can be communicated to the second lumen 120 over the entire circumference thereof at the proximal end of the space 112. In this way, since the second lumen having a relatively large capacity is communicated at the proximal end of the balloon 11, it can be relatively easy to charge a fluid from the second lumen into the balloon 11. The balloon 11 can be an exemplary balloon described herein. In FIG. 3, the balloon 11 can be constituted of a three-layered film, but is not limited thereto. The balloon can be formed of two or more layers including at least a hard layer and flexible layer as stated herein.

In order to confirm the position of a tubular film body of the balloon 11 by X-ray contrast study, at least one X-ray marker can be provided on the outer surface of the inner tube 14. The X-ray marker can have opposite end portions at a position in the vicinity of a rear end side as viewed from the fixed portion between the balloon 11 and the inner tube 14 and also at a position in the vicinity of the distal end as viewed from the fixed portion between the balloon 11 and the outer tube 12, for example, at portions corresponding to the opposite ends of the tubular film body 2 of the balloon 11 and can have a length equal to the length of the tubular film body 2 of the balloon 11.

The X-ray marker can be formed of an X-ray opaque material (for example, gold, platinum, tungsten or alloys thereof, or a silver-palladium alloy). The marker can be in the form of a coil spring, for example, densely coiled by 1 to 4 mm, for example, 2 to 3 mm, from the opposite ends of the marker, respectively. This is because, for example, the position of the balloon 11 can be confirmed under X-ray guidance. When formed as a spring, the marker can serve as a reinforcing body for preventing the inner tube located within the balloon from creating kinks and collapsing at the bent portions thereof.

If the marker is formed of a single spring coil and wound about the outer periphery of the inner tube 14 in intimate contact therewith, the proof strength against an outer force can become stronger. If a coil wire body is shaped to provide a circular, square or ellipsoidal section, the proof strength against an outer force can become much stronger.

The hub 13 can have a second opening 130 communicating with the second lumen 120 and forming an injection port that is an inlet of a pathway of charging or discharging a fluid and an outer tube hub fixedly secured to the outer tube 12. As mentioned above, the hub 13 can have the opening 130 communicating with the second lumen 120, for which the second opening 130 also serves for a flow passage. For example, the opening is communicated to fluid charge and discharge units (not shown) such as an indeflator, a syringe, a pump and the like. When using these units, a fluid is charged into the balloon 11 via the opening 130 and second lumen 120 or is discharged from the balloon 11. For example, the opening 130 and lumen 120 function as a charge and discharge path of a drive fluid capable of inflating or deflating the balloon 11.

As a material for the hub, mention is made, for example, of a thermoplastic resin such as polycarbonate, polyamide, polysulfone, polyallylate, methacrylate-butylene-styrene copolymer or the like.

As a material for the outer tube hub, mention is made, for example, of a thermoplastic resin such as polycarbonate, polyamide, polysulfone, polyallylate, methacrylate-butylene-styrene copolymer or the like.

In FIG. 3, an instance of the hub 13 is illustrated wherein there is shown, without provision of a branched hub, the rapid exchange type hub, in which the first lumen and the second lumen are, respectively, attached liquid-tightly, for example, with a tube having a port member formed with an opening at a rear end thereof. The hub 13 may be of the over-the-wire type wherein a branched hub is provided at the hub 13.

EXAMPLES

Example 1

A 30 μm thick polyamide (PA) resin sheet (commercial name: L25, made by EMC Inc.) and a 30 μm thick polyamide elastomer resin sheet (commercial name: Grilflex ELG5660 with a Shore D hardness of 56 and a polyamide block ratio of 67 wt %, made by EMS Inc.) were subjected to thermocompression by means of a heat press at a temperature of 170° C. and a compression pressure of 2.5 MPa for 60 seconds to obtain a double-layered sheet (60 μm in thickness). The adhesion force between the bonded sheets of the thus obtained double-layered sheet was measured according to a peel adhesion strength testing method/Part 3: T-type peeling test (JIS 6854-3), revealing that no peeling occurred at a peel strength of 5.0 N/mm.

Example 2

A test was carried out in the same manner as in Example 1 using a 30 μm thick polyamide (PA) resin sheet (commercial name: L25, made by EMC Inc.) and a 30 μm thick polyamide elastomer resin sheet (commercial name: Grilflex ELG6260 with a Shore D hardness of 62 and a polyamide block ratio of 85 wt %, made by EMS Inc.), with the result that no peeling occurred at a peel strength of 5.0 N/mm.

Example 3

A 30 μm thick polyamide (PA) resin sheet (commercial name: L25, made by EMC Inc.) and a 30 μm thick polyamide elastomer resin sheet (with a mixing ratio by weight of ELG5660/ELG6260 of 3/7, a Shore D hardness of 60 and a polyamide block ratio of 81 wt %) were subjected to thermocompression by means of a heat press at a temperature of 170° C. and a compression pressure of 2.5 MPa for 60 seconds to obtain a double-layered sheet (60 μm in thickness). The adhesion strength between the bonded sheets of the thus obtained double-layered sheet was measured according to a peel adhesion strength testing method/Part 3: T-type peeling test (JIS 6854-3), revealing that no peeling occurred at a peel strength of 5.0 N/mm.

Example 4

A test was carried out in the same manner as in Example 1 using a 30 μm thick polyamide (PA) resin sheet (commercial name: L25, made by EMC Inc.) and a 30 μm thick polyamide elastomer resin sheet (with a mixing ratio by weight of ELG5660/ELG6260 of 5/5, a Shore D hardness of 58 and a polyamide block ratio of 76 wt %), with the result that no peeling occurred at a peel strength of 5.0 N/mm.

Example 5

A test was carried out in the same manner as in Example 1 using a 30 μm thick polyamide (PA) resin sheet (commercial name: L25, made by EMC Inc.) and a 30 μm thick polyamide elastomer resin sheet (with a mixing ratio by weight of ELG4960/ELG5660 of 3/7, a Shore D hardness of 60 and a polyamide block ratio of 54 wt %), with the result that no peeling occurred at a peel strength of 5.0 N/mm.

Comparative Example 1

A test was carried out in the same manner as in Example 1 using a 30 μm thick polyamide (PA) resin sheet (commercial name: L25, made by EMC Inc.) and a 30 μm thick polyamide elastomer resin sheet (commercial name: PEBAX5533 with a Shore D hardness of 55 and a polyamide block ratio of 59 wt %, made by Arkema Inc.), with the result that the peel strength was at 3.4 N/mm.

From the results of the tests of Examples 1, 2, 3, 4, 5 and Comparative Example 1, it was found that as to the polyamide elastomer to be bonded with the polyamide resin (L25), the sheets made of the polyamide elastomers having higher percentages by weight of the repeating units of the polyamide block became higher in adhesion force.

Three-layered balloons made of a polyamide layer and polyamide elastomer layers were made, and the respective PA three-layered balloons were evaluated with respect to the pressure resistance and hardness.

Example 6

A co-extrusion process using a wire coating technique was carried out to make a three-layered tube including an outer layer and an inner layer, each made of ELG5660 (commercial name: Grilflex with a polyamide block ratio of 67 wt % and a Shore D hardness of 56, made by EMS Inc.) and an intermediate layer made of L25.The inner diameter of the inner layer and the outer diameters of the inner layer, intermediate layer and outer layer tubes were, respectively, at 0.35 mm, 0.47 mm, 0.82 mm and 0.9 mm. This three-layered tube was placed in a mold of a given shape, shown in FIG. 2, and annealed, followed by blow molding to provide a desired balloon. The blow molding conditions of the balloon included 90° C. and 4.2 MPa. Thereafter, the pressure resistance test (i.e., a load was measured by autograph at the time when a balloon inflated under a given pressure was pressed with a projection and was burst) was carried out, revealing that the burst pressure was at 32.1 MPa and a value of burst pressure/film thickness was at 1.77 (MPa/μm). The hardness was evaluated according to the method described in ISO 868.

Example 7

In the same manner as in Example 6, there was made a three-layered tube wherein the outer and inner layers were each made of ELG6260 (commercial name: Grilflex with a polyamide block ratio of 85 wt % and a Shore D hardness of 62, made by EMS Inc.) and the intermediate layer was made of L25.The inner diameter of the inner layer of the three-layered tube and the outer diameters of the inner layer, intermediate layer and outer layer tubes were, respectively, at 0.36 mm, 0.48 mm, 0.82 mm and 0.9 mm. A balloon was made by blow molding in the same manner as in Example 6.The blow molding conditions of Example 7 included 100° C. and 3.3 MPa. The pressure resistance test (i.e., a load was measured by autograph at the time when a balloon inflated under a given pressure was pressed with a projection and was burst) was carried out, revealing that the burst pressure was at 35.1 MPa and a value of burst pressure/film thickness was at 1.83 (MPa/μm). The hardness was evaluated according to the method described in ISO 868.

Comparative Example 2

In the same manner as in Example 6, there was made a three-layered tube wherein the outer and inner layers were each made of PEBAX5533 (commercial name: PEBAX with a polyamide block ratio of 59 wt % and a Shore D hardness of 55, made by Arkema Inc.) and the intermediate layer was made of L25.The inner diameter of the inner layer of the three-layered tube and the outer diameters of the inner layer, intermediate layer and outer layer tubes were, respectively, at 0.37 mm, 0.48 mm, 0.82 mm and 0.9 mm. A balloon was made by blow molding in the same manner as in Example 6.The blow molding conditions included 100° C. and 3.3 MPa. As a result of the pressure resistance test, it was revealed that the burst pressure was at 22.8 MPa and a value of burst pressure/film thickness was at 1.11 (MPa/μm).

In view of the results of Examples 6, 7 and Comparative Example 2, it was clarified that higher weight percentages of the repeating units of the polyamide block in the polyamide elastomer bonded to the polyamide layer (L25) led to a more improved pressure resistance. For example, the polyamide elastomer having a higher weight percentage of the repeating units of the polyamide block can be thermally bonded with the polyamide layer more strongly, thereby improving the adhesion force.

Example 8

The balloon (with an outer diameter of 3 mm and a length of 15 mm) described in Example 7 was shaped as a product and evaluated with respect to lesion passage thereof by use of a guide wire (commercial name: Runthrough NS, made by Terumo Corporation). In-depth accessibility to a pseudo tortuous blood vessel was evaluated by use of a commercially available flexure model (PTCA Trainer & Technical Guide, published by Medical Sense Ltd.), resulting in arrival at up to R13. Thus, indentation performance, flexibility, following performance and kink resistance were good.

Example 9

The balloon (with an outer diameter of 3 mm and a length of 15 mm) described in Example 7 was shaped as a product and evaluated with respect to lesion passage thereof by use of a guide wire (commercial name: Runthrough NS, made by Terumo Corporation). In-depth accessibility to a pseudo tortuous blood vessel was evaluated by use of a commercially available flexure model (PTCA Trainer & Technical Guide, published by Medical Sense Ltd.), resulting in arrival at up to R13. Thus, indentation performance, flexibility, following performance and kink resistance were good.

Comparative Example 3

In the same manner as in Comparative Example 2, there was made a three-layered tube including an outer and inner layers, each made of PEBAX6333(commercial name: PEBAX with a polyamide block ratio of 79 wt % and a Shore D hardness of 63, made by Arkema Inc.) and an intermediate layer made of L25 (wherein the inner diameter of the inner layer and the outer diameters of the inner, intermediate and outer layer tubes were, respectively, at 0.37 mm, 0.48 mm, 0.82 mm and 0.9 mm). Thereafter, a balloon (with an outer diameter of 3 mm and a length of 15 mm), which was made by blow molding under blow molding conditions of 100° C. and 3.3 MPa, was shaped as a product and the lesion passage thereof was evaluated by use of a guide wire (commercial name: Runthrough NS, made by Terumo Corporation). Such a model as indicated above was used to evaluate in-depth accessibility to a pseudo tortuous blood vessel, revealing arrival only at up to R16. Thus, the indentation performance, flexibility, following performance and kink resistance were not as good as those of Examples 8 and 9.

From the above results of Examples 8, 9 and Comparative Example 3, it was found that when using the balloons having the outer layer of the polyamide elastomer whose hardness is lower, the passage capability becomes good. While not wishing to be bound to any particular theory, it is believed that when the hardness of the outer layer is high, the force of collision (friction) between the balloon and the pseudo tortuous blood vessel becomes high.

What is claimed is:

1. A balloon for a catheter, comprising:
a film body that is inflatable and deflatable by a fluid supplied from a catheter,
wherein said film body includes a hard layer containing a polyamide and a flexible layer formed on the hard layer and containing a polyamide elastomer having a Shore D hardness that is 56 to 62, and a content of amide units of the polyamide elastomer in the flexible layer is not less than 60 wt %,
wherein the amide units of the polyamide elastomer in the flexible layer include repeating units of at least one of the following formula (1) or (2):

in which n is an integer of 5 to 11;

in which a is an integer of 4 to 12 and b is an integer of 4 to 10.

2. The balloon for a catheter according to claim 1, wherein the film body comprises a connection portion axially extending from an end of said film body, wherein the connection portion is capable of being connected to the catheter.

3. The balloon for a catheter according to claim 1, wherein said polyamide elastomer is made of at least one polyamide block copolymer represented by the following formula (3) or (4):

in which a is an integer of 4 to 12, b is an integer of 4 to 10, c is an integer of 0 to 100, d is an integer of 0 to 100, p is an integer of 2 to 4, q is an integer of 1 to 100, and Ln is a linker moiety represented by —C(O)—R—C(O)— wherein R represents an alkylene group having 2 to 12 methylene units;

in which n is an integer of 5 to 11, m is an integer of 0 to 100, l is an integer of 0 to 100, p is an integer of 2 to 4, q is an integer of 1 to 100, and L is a linker moiety represented by —C(O)—R—C(O)—wherein R represents an alkylene group having 2 to 12 methylene units.

4. The balloon for a catheter according to claim 3, wherein R in formula (3) or (4) is selected from the group consisting of: a tetramethylene group, a 2-methylpropylene group, a 1,1-dimethylethylene group, an n-pentylene group, an n-hexylene group, an n-nonylene group, a 1-methyloctylene group, a 6-methyloctylene group, a 1-ethylheptylene group, a 1-(n-butyl)pentylene group, a 4-methyl-1-(n-propyl)pentylene group, a 1,5,5-trimethylhexylene group, a 1,1,5-trimethylhexylene group, an n-decylene group, a 1-methylnonylene group, a 1-ethyloctylene group, a 1-(n-butyl)hexylene group, a 1,1-dimethyloctylene group, a 3,7-dimethyloctylene group, an n-undecylene group, and a 1-methyldecylene group.

5. The balloon for a catheter according to claim 1, wherein the flexible layer includes a first flexible layer and a second flexible layer, wherein the first flexible layer is attached to a surface of the hard layer and is in intimate contact with the surface of the hard layer, and the second flexible layer is attached to an opposite surface of the hard layer and is in intimate contact with the opposite surface of the hard layer.

6. The balloon for a catheter according to claim 1, wherein the flexible layer is in intimate contact with a surface of the hard layer.

7. The balloon for a catheter according to claim 1, wherein an average thickness of the flexible layer is 0.5 to 10 μm.

8. The balloon for a catheter according to claim 1, wherein an average thickness of the hard layer is 0.5 to 49.5 μm.

9. The balloon for a catheter according to claim 1, wherein the amide units of the polyamide elastomer contained in the flexible layer and polymer chains of the polyamide contained in the hard layer, are bonded together.

10. The balloon for a catheter according to claim 1, wherein the flexible layer and the hard layer are subjected to thermocompression bonding.

11. The balloon for a catheter according to claim 1, wherein a weight-average molecular weight of the polyamide elastomer is $1.0 \times 10^4$ to $1.0 \times 10^5$.

12. The balloon for a catheter according to claim 1, wherein the polyamide is made of at least one selected from the group consisting of nylon 11, nylon 12 and nylon 6.12.

13. A balloon catheter, comprising the balloon for a catheter according to claim 1, and a catheter.

14. A balloon catheter, comprising:
an inner tube having a first lumen opened at a distal end thereof;
an outer tube coaxially provided with said inner tube, having a distal end distance from the distal end of said inner tube toward a proximal end at a given length, and having a second lumen between an outer surface of said inner tube and the outer tube;
a hub having an opening communicating with said second lumen; and
a balloon fixed to said inner tube at a distal end thereof, fixed to said outer tube at a proximal end thereof, and communicating in the inside thereof with said second lumen, wherein a fluid is charged or discharged from said opening to inflate or deflate said balloon,
wherein the balloon comprises a film body, wherein said film body includes a hard layer containing a polyamide and a flexible layer formed on the hard layer and containing a polyamide elastomer having a Shore D hardness that is 56 to 62, and a content of amide units of the polyamide elastomer in the flexible layer is not less than 60 wt %,
wherein the amide units of the polyamide elastomer in the flexible layer include repeating units of at least one of the following formula (1) or (2):

in which n is an integer of 5 to 11;

in which a is an integer of 4 to 12 and b is an integer of 4 to 10.

15. The balloon catheter according to claim 14, wherein said polyamide elastomer is made of at least one polyamide block copolymer represented by the following formula (3) or (4):

in which a is an integer of 4 to 12, b is an integer of 4 to 10, c is an integer of 0 to 100, d is an integer of 0 to 100, p is an integer of 2 to 4, q is an integer of 1 to 100, and Ln is a linker moiety represented by —C(O)—R—C(O)— wherein R represents an alkylene group having 2 to 12 methylene units;

in which n is an integer of 5 to 11, m is an integer of 0 to 100, l is an integer of 0 to 100, p is an integer of 2 to 4, q is an integer of 1 to 100, and L is a linker moiety represented by —C(O)—R—C(O)—wherein R represents an alkylene group having 2 to 12 methylene units.

16. The balloon catheter according to claim 14, wherein the flexible layer includes a first flexible layer and a second flexible layer, wherein the first flexible layer is attached to a surface of the hard layer and is in intimate contact with the surface of the hard layer, and the second flexible layer is attached to an opposite surface of the hard layer and is in intimate contact with the opposite surface of the hard layer.

17. The balloon catheter according to claim 14, wherein the amide units of the polyamide elastomer contained in the flexible layer and polymer chains of the polyamide contained in the hard layer, are bonded together.

18. The balloon catheter according to claim 14, wherein the flexible layer and the hard layer are subjected to thermocompression bonding.

* * * * *